United States Patent [19]

Kopp et al.

[11] 4,351,800
[45] Sep. 28, 1982

[54] THIN LAYER PLATE CHROMATOGRAPHY APPARATUS

[75] Inventors: Reiner H. Kopp, Centerport; Allen I. Panetz, Huntington, both of N.Y.

[73] Assignee: Biochemical Diagnostics, Inc., Farmingdale, N.Y.

[21] Appl. No.: 232,134

[22] Filed: Feb. 6, 1981

[51] Int. Cl.³ .................. G01N 1/14; G01N 31/08
[52] U.S. Cl. .................... 422/70; 141/130; 422/65; 422/100; 422/104
[58] Field of Search .............. 422/70, 100, 104, 65; 141/130

[56] References Cited

U.S. PATENT DOCUMENTS

| | | | |
|---|---|---|---|
| 3,189,413 | 6/1965 | Davis | 422/70 |
| 3,667,917 | 6/1972 | Brandt | 422/70 X |
| 3,766,884 | 10/1973 | Rosenthal | 422/70 X |
| 3,833,341 | 9/1974 | Tocci | 422/70 |
| 3,843,053 | 10/1974 | Thoden | 422/70 X |
| 4,272,381 | 6/1981 | Kremer | 422/70 X |

Primary Examiner—Ronald E. Serwin
Attorney, Agent, or Firm—Eisenman, Allsopp & Strack

[57] ABSTRACT

There is disclosed apparatus for rapidly transferring samples for analysis by thin layer chromatography from a sample container to the chromatography plate and in which a chromatography plate is supported in a housing through which drying air, preferably heated, passes over the working surface of the chromatography plate. A plurality of sample applicators are precisely positioned above the plate by means of a transverse mounting plate having a transverse array of holes through which the applicators are passed to engage the working surface of the plate, the applicators taking the form of an imperforate sleeve surrounding a porous core projecting from the end of the sleeve and sharpened to a point to minimize exposure, with the other end of the sleeve projecting beyond the inner end of the porous core to define a solvent reservoir which if desired can be packed with fiber wadding to control fluid flow and with the reservoir adapted to be closed by a sealing cover member.

6 Claims, 5 Drawing Figures

THIN LAYER PLATE CHROMATOGRAPHY APPARATUS

BACKGROUND OF THE INVENTION

Thin layer chromatography, referred to in laboratory parlance as TLC, has become an increasingly useful tool for detecting tiny amounts of drugs in specimens. The analysis procedure involves the transfer of specimens to be analyzed to a spot on the chromatography plate, drying the deposition, and thereafter activating plate with solvent to initiate the detectable migration patterns on the plate surface thus revealing the identity of the compounds or drugs contained in the specimen. In this fashion urine samples are screened for barbituates, opiates, amphetamines and other narcotics. Equipment and techniques heretofore available have made the screening of multiple samples both expensive and time-consuming. The present invention has for its objectives to provide a new design for an applicator for picking up, as by absorption or adsorption, a specimen to be analyzed and carrying it quickly to the TLC plate. Another objective of the invention is to provide a means for accommodating a large number of supporting applicators on one plate at precisely defined locations and for the controlled drying of both the deposited spots and the subsequent solvent saturation.

THE PREFERRED EMBODIMENT

Figure 1:
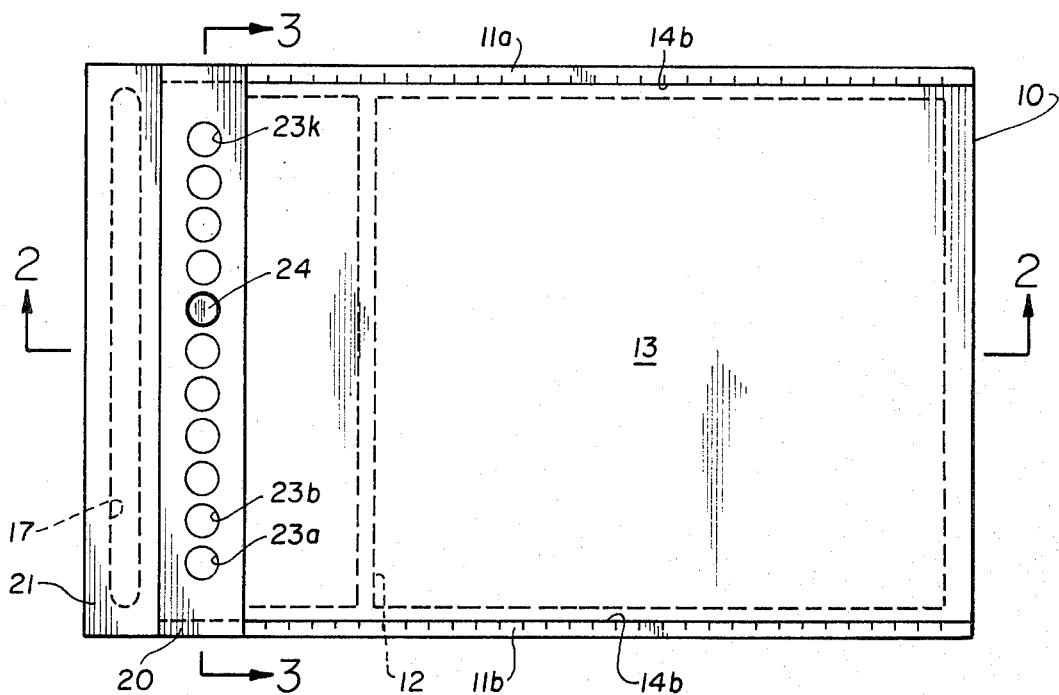
FIG. 1 is a top view of a thin layer chromatography plate supporting and processing apparatus formed in accordance with the present invention.
Figure 2:
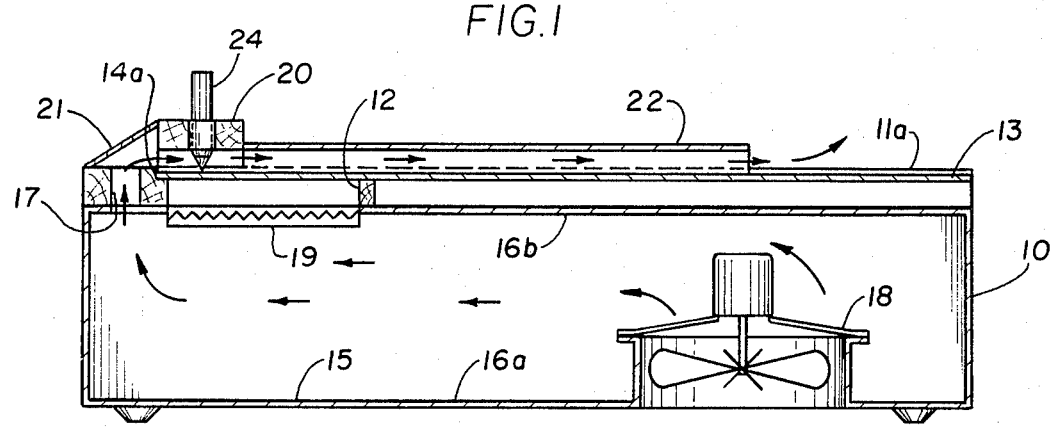
FIG. 2 is a view in vertical longitudinal section taken on line 2—2 of FIG. 1 looking in the direction of the arrows.
Figure 3:
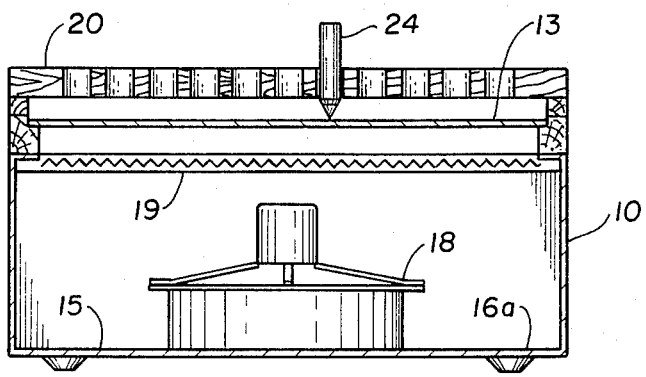
FIG. 3 is a view in vertical transverse section taken on line 3—3 of FIG. 1 looking in the direction of the arrows.

Referring to FIGS. 1-3, there is shown a thin layer chromatography (TLC) plate supporting and processing apparatus comprising a housing 10 having calibrated side rails 11a and 11b extending longitudinally, and a transverse rail 12 which together constitute the supports for a TLC plate 13. The plate 13 is accurately positioned within the housing by means of stops 14a and 14b near the forward end of the unit and disposed in the plane of mounting of the plate.

The hollow body of the housing defines an internal chamber 15 bounded by a bottom 16a vented to the atmosphere and a top 16b. The chamber 15 is placed in communication with the TLC plate 13 by means of an air slot 17 formed at one end of the top 16b. A fan assembly 18 draws ambient air into the housing through the vented bottom where it is warmed by an electrical resistance heating pad 19 secured to the under surface of the top 16b at a point close to the air slot and precisely beneath the area of the TLC plate where spotting occurs, all as described below.

The transverse sample applicator holder 20 is supported near the end of the housing adjacent the air slot 17, with the air being directed from the slot into the horizontal space between the underside of the applicator holder 20 and the upper surface of the TLC plate by a baffle plate 21. If desired, the horizontal flow path between the TLC plate can be increased in length by a removable lid 22 abutting the edge of the applicator holder. The applicator holder 20 is formed with an array of holes 23a, 23b . . . 23k adapted to receive sample applicators 24 which are adapted to engage the surface of the TLC plate to deposit or "spot" specimens thereon for chromatographical analyses.

Figure 4:
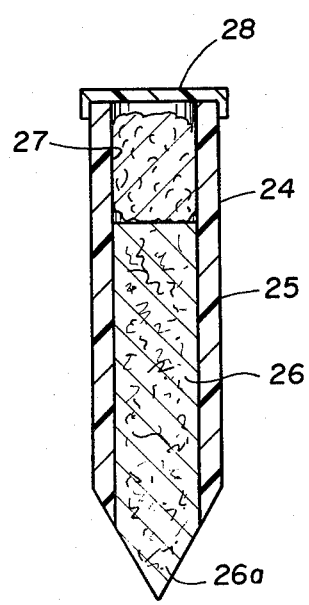
FIG. 4 is a view of vertical section in enlarged scale of a spotting applicator for use in the apparatus of FIGS. 1-3.

Referring to FIG. 4, the applicator 24 (shown in enlarged scale) includes an imperforate cylindrical sheath 25 preferably formed of plastic, such as polyethylene or polypropylene, into which is fitted a core 26 of porous material which in the embodiment of FIG. 4 can take the form of porous polyethylene having a pore size of 5 to 10 microns. The tip 26a is sharpened to define a point and to limit the area of the porous core exposed to free air. The tip is preferably designed to deposit a small spot of solvent and specimen on the plate 13, typically 0.5 to 1.0 cm. in diameter. The sheath 25 extends beyond the inner end of the core to define a solvent reservoir 27 which can be sealed by a removable cap 28. If desired, the reservoir can include a packed cotton wad to control the flow of liquid solvent through the core.

To carry out an analysis, the sample is first dissolved in a volatile organic solvent. The sample is picked up by the applicator by immersing the exposed tip into the dissolved sample. It is important at this stage that the solvent bearing the sample not spread through the entire length of the core 26 but that the absorption terminate before the material spreads into the cotton pack in the solvent reservoir 27. After removal from the sample source, the sample applicator 24 is then placed in one of the mounting holes 23a . . . 23k of the applicator holder 20 to position the pointed tip of the applicator on the surface of the TLC plate 13 in a precisely defined position. An aliquot of organic solvent, typically 20 to 400 microliters, is pipetted into the reservoir which can then be covered or left open as desired. The packed cotton slowly releases the solvent in the reservoir, allowing it to travel downward through the porous core 26 carrying the sample with it onto the TLC plate. Alternatively, the dissolved sample can be placed directly on the cotton pack in the solvent reservoir 27, this being followed by an aliquot of organic solvent in a manner described in the preceding paragraphs. As stated above, the sample is deposited in a small spot, typically 0.5 to 1.0 cm. in diameter. The exact spot size is determined by the TLC plate temperature, which is controlled by the electrical resistor heating pad 19 mounted close to the under side of the plate, the forced air-flow volume derived from the fan 18 and passed through the air slot 17 to flow over the TLC plate in the narrow channel defined by the baffle 21 and the under side of the transverse applicator holder 20, and the volatility of the solvent.

With the spot size and position now defined and the specimen to be analyzed free of its initial solvent vehicle, the TLC plate with its array of sample spots can then be removed from its support and the lower edge dipped into a chromatography solvent in accordance with standard procedures, after which the specimens with their unknown compound contents migrate upwardly along the plate surface. After a predetermined time interval, the plate can be removed from the chromatography solvent and returned to the supporting apparatus where the calibrations in the side rails 11a and 11b will indicate how far up the plate the unknown material solvent traveled. The apparatus can also be used to drive off the TLC solvents from the plate, to heat it via the heating pad 19 or to cool it by means of the air currents, all as might be required for chemical reactions to occur on the plate surface. It will be understood that the lid or cover 22 is not used for later stages of the process.

Figure 5:
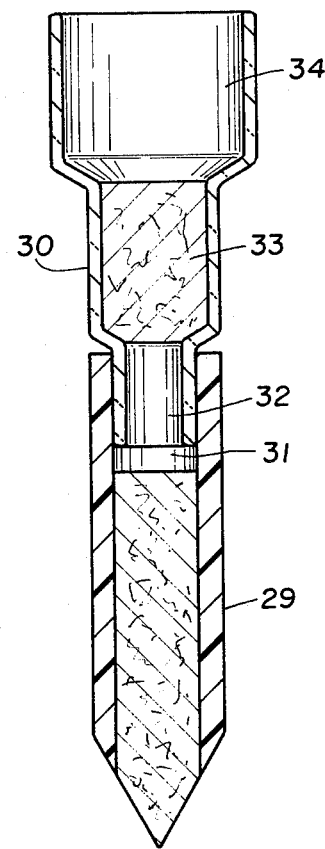
FIG. 5 is a view in vertical section of a spotting applicator assembly utilizing portions of the spotter of FIG. 4.

While the invention has been described having reference to preferred embodiments, it will be understood that it can take various other forms and arrangements within the scope of the invention. For example, the core of the sample applicator can constitute a paper wick or porous medium containing ion exchangers to selectively hold back compounds from elution. Also, immobilized antibodies, enzymes or other reactant compounds may be incorporated into the porous media as an aid in gaining more sample selectivity. As shown in FIG. 5, an applicator 29 of generally similar configuration to that shown in FIG. 4 is used with a chromatography column 30 inserted into the upper space 31 corresponding to the reservoir 27 of FIG. 4. The column 30 includes in addition to its depending tip 32 inserted into the space 31, a sample holding chamber containing an absorbent material 33, such as Amberlite XAD-2, surmounted by a solvent reservoir 34. The invention should not, therefore, be regarded as limited except as defined in the following claims.

We claim:

1. Apparatus for the application of specimens to thin layer chromatography plates comprising a housing for supporting one or more plates, positioning stops for locating the plates in a precisely predetermined position, a holder for specimen applicators disposed above the plane of the plate and extending transversely across one end portion thereof and disposed in close proximity to the plane to define an air channel along the top surface of the plate and through which the tip portions of the applicators pass to reach the chromatography plate, said holder including means to mount a plurality of specimen applicators across the width of the plate, air duct means connecting the air channel to the interior of the housing and means in the housing to impel air through the air duct and air channel to pass around the tip portions of the applicators.

2. Apparatus as set forth in claim 1 including heater means beneath the plane of the plate at the end portion below the points of application of the specimens and in close proximity to the underside of the plates.

3. Apparatus as set forth in claim 2, said means to impel air including a fan in the housing to direct air past the heating means prior to entering the channel between the plates and the holder for the applicators.

4. Apparatus as set forth in claim 1 including at least one calibrated side rail extending longitudinally along one edge of the plate mounted in the housing.

5. Apparatus as set forth in claim 4 including two calibrated side rails disposed respectively along opposite longitudinally edges of the plate, said side rails also constituting supports for the edges of the plate.

6. Apparatus as set forth in claim 3, said air duct being located at a point beyond the ends of the plates adjacent the area of specimen application, and baffle means cooperating with said applicator holding means to direct the flow of air through the channel between the applicator mounting means and the upper surface of the plates.

* * * * *